US00PP28873P3

(12) United States Plant Patent
Randag

(10) Patent No.: US PP28,873 P3
(45) Date of Patent: Jan. 9, 2018

(54) VARIETY OF CALLA LILY PLANT NAMED 'HELVETIA'

(50) Latin Name: *Zantedeschia sprengeri*
Varietal Denomination: Helvetia

(71) Applicant: Sande B.V., 't Zand (NL)

(72) Inventor: Cecilius Jan-Jochem Randag, 't Zand (NL)

(73) Assignee: Sande B.V., 't Zand (NL)

( * ) Notice: Subject to any disclaimer, the term of this patent is extended or adjusted under 35 U.S.C. 154(b) by 53 days.

(21) Appl. No.: 14/998,492

(22) Filed: Jan. 12, 2016

(65) Prior Publication Data

US 2016/0212924 P1 Jul. 21, 2016

Related U.S. Application Data

(60) Provisional application No. 62/125,226, filed on Jan. 15, 2015.

(51) Int. Cl.
*A01H 5/02* (2006.01)

(52) U.S. Cl.
USPC ..... Plt./490

(58) Field of Classification Search
USPC ..... Plt./490
CPC ..... A01H 5/0272
See application file for complete search history.

*Primary Examiner* — Kent L Bell
(74) *Attorney, Agent, or Firm* — The Webb Law Firm

(57) ABSTRACT

'Helvetia' is a new variety of calla lily plant having inflorescences with a white-colored spathe that produces 4-20 inflorescences per tuber. The height of the top of an inflorescence above the soil can reach up to 40 cm, and the leaves are dark green with transparent maculations present and have a leathery texture.

2 Drawing Sheets

Botanical classification: *Zantedeschia sprengeri.*
Varietal denomination: 'HELVETIA'.

BACKGROUND OF THE NEW PLANT

The present invention comprises a new and distinct cultivar of calla lily, botanically known as *Zantedeschia sprengeri* and hereinafter referred to by the cultivar name 'Helvetia'.

'Helvetia' is a product of a planned breeding program, which had the objective of creating *Zantedeschia* hybrids for pot flower production in a wide range of colors with a large, classic flower shape. The breeding program began in 1989, and the new cultivar is a seedling selected from the crossing of a *Zantedeschia sprengeri* selection referred to as Z030636 (female parent, unpatented) with *Zantedeschia sprengeri* 'Swan Lake' (male parent, U.S. Plant Pat. No. 15,664). 'Helvetia' was selected in 2008 by the inventor in 't Zand, The Netherlands as one flowering plant within the progeny of the stated cross.

The first act of asexual reproduction of 'Helvetia' by tissue culture was performed by the inventor in September of 2010 in 't Zand, The Netherlands. Subsequent asexual reproductions by tissue culture at the same location have demonstrated that the combination of characteristics as herein disclosed for the new cultivar are retained and reproduced true to type through successive generations of asexual reproduction.

The following observations, measurements and comparisons describe plants grown in 14 cm pots in 't Zand, The Netherlands under greenhouse conditions, which approximate those generally used in horticultural practice. Color references are made to The 2001 R.H.S. Colour Chart of The Royal Horticultural Society of London, except where general color terms of ordinary significance are used.

The present invention has not been evaluated under all possible environmental conditions. The phenotype may vary with variations in environment without a change in the genotype of the plant.

The following traits have been repeatedly observed and determined to be basic characteristics of 'Helvetia' which, in combination, distinguish this calla lily as a new and distinct cultivar:

1. White-colored spathe with no pink blush color present;
2. Green leaves with a few linear white spots; and
3. High inflorescence production.

Further, when compared to calla lily plant named 'Captain Ventura' (U.S. Plant Pat. No. 21,245), 'Captain Ventura' has a mature outer surface spathe color that varies between White Group RHS 155C and Green-White Group RHS 157D with a Green Group RHS 143A outer tip, whereas the upper surface spathe color of 'Helvetia' varies between White Group RHS 155A and 155D.

Table 1 provides similarities and differences of 'Helvetia' to its parents, *Zantedeschia sprengeri* selection Z030636 and *Zantedeschia sprengeri* 'Swan Lake'.

TABLE 1

| 'Helvetia' | Similarities | Differences |
|---|---|---|
| Z030636 | Spathe color | Absence of pink blush color in spathe |
| | Spathe shape | Plant height |
| 'Swan Lake' | Absence of pink blush color in spathe | Spathe shape |
| | Spathe color | Number of inflorescences |
| | | Plant height |

BRIEF DESCRIPTION OF THE DRAWINGS

The accompanying photographic drawings illustrate the new variety, with the colors being as nearly true as is possible with color illustrations of this type.

DESCRIPTION OF THE NEW PLANT

The Plant

Figure 1:
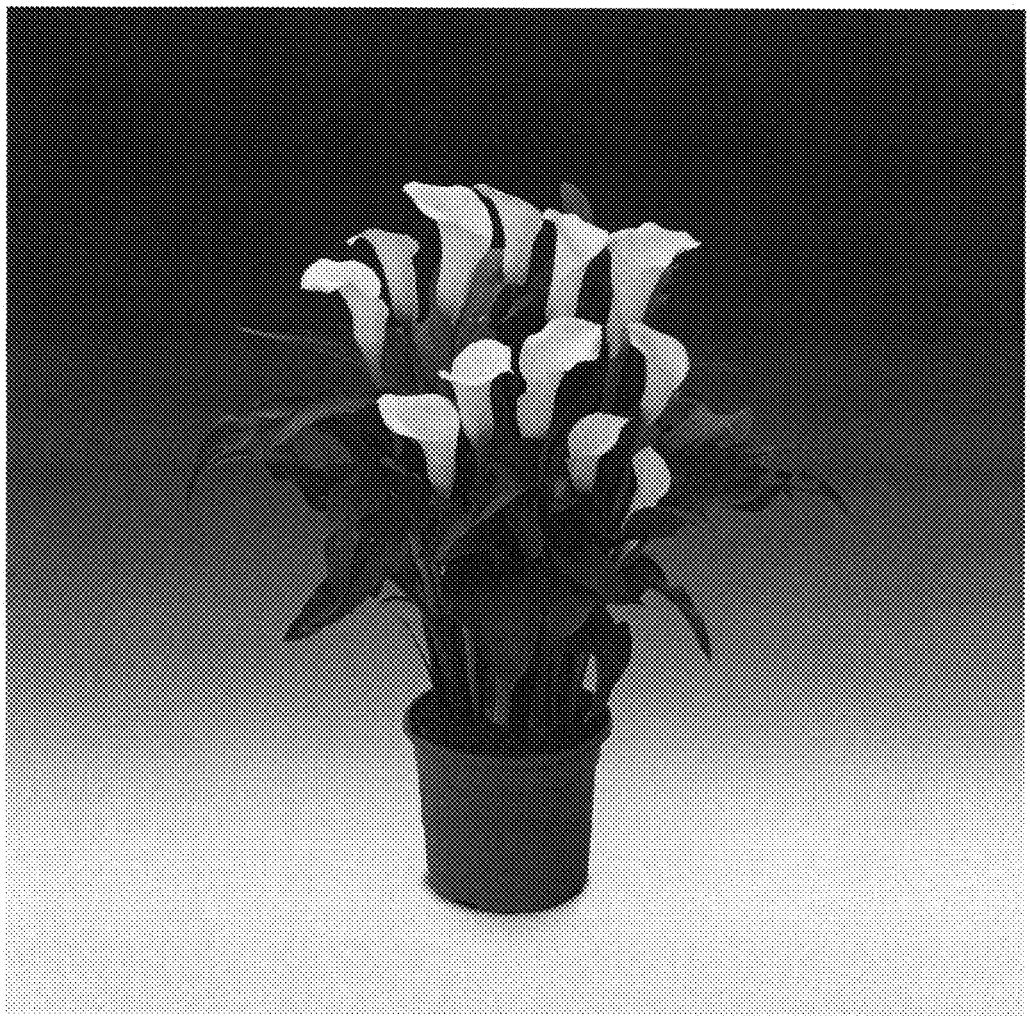
FIG. 1 is a photograph of a plant of the new variety at the early stage of flowering.
Figure 2:
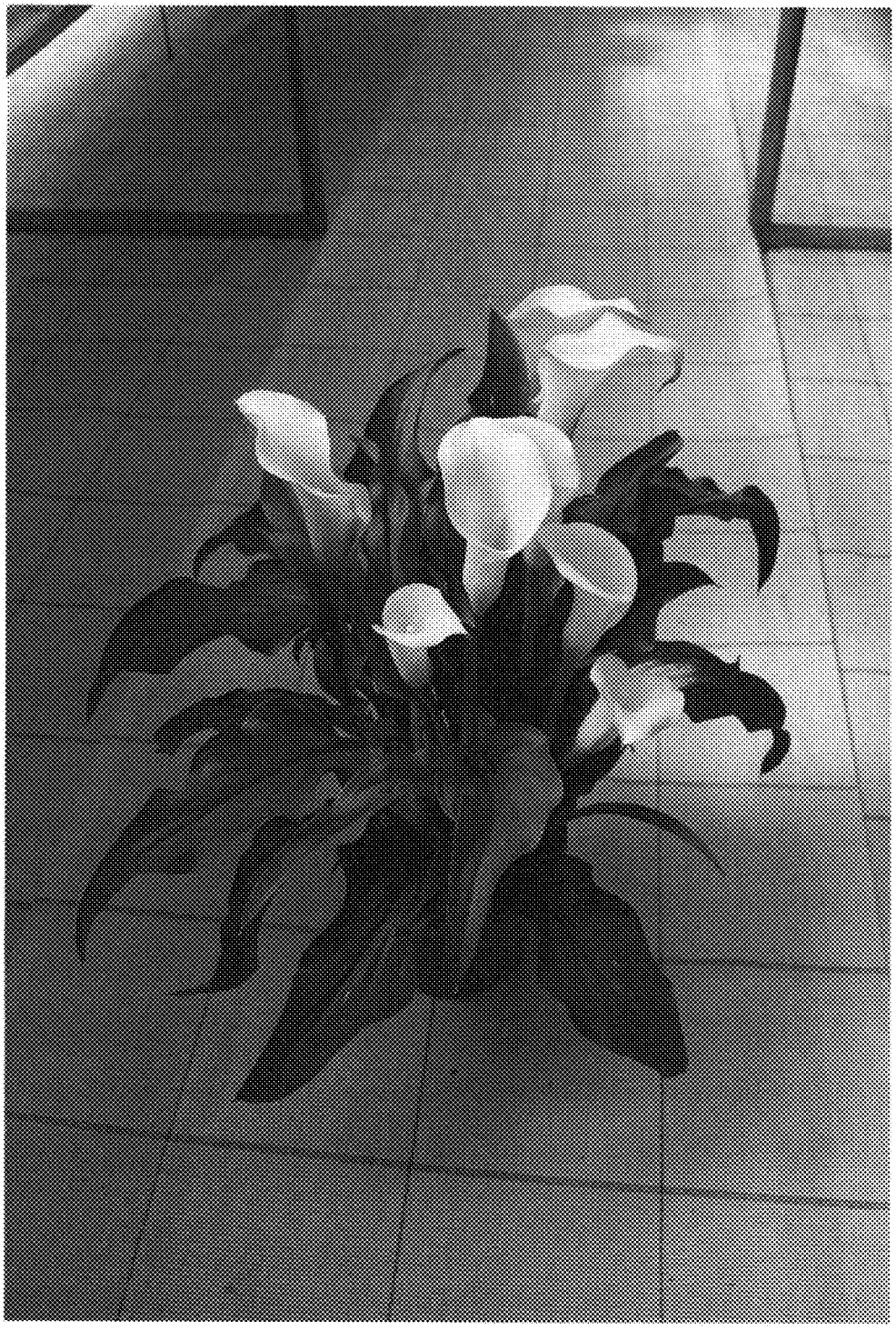
FIG. 2 is a photograph of a plant of the new variety at the later stage of flowering.

Size:
- *Height of the leaf canopy above the soil.*—7-38 cm.
- *Height of top of inflorescence above the soil.*—12-40 cm.
- *Diameter.*—20-50 cm.

Form: Erect.

Number of inflorescences per tuber:
- *Size* 14-16 *cm in diameter.*—4-8 inflorescences.
- *Size* 16-18 *cm in diameter.*—7-15 inflorescences.
- *Size* 18-20 *cm in diameter.*—10-20 inflorescences.

Branches:
- *Character.*—Many; like the variety 'Odessa' (U.S. Plant Pat. No. 18,833).
- *Color.*—Between Green Group RHS 137A and Brown Group RHS 200A.

Leaves:
- *Size.*—Width: 2-8 cm. Length: 7-20 cm.
- *Number per plant.*—20-40.
- *Shape.*—Lanceolate.
- *Color.*—Upper surface: Green Group RHS 139A to 139B, having transparent maculations between White Group RHS 155B and N155A. Lower surface: Green Group RHS 137A to 137B, having transparent maculations between White Group RHS 155B and N155A.
- *Apex.*—Apiculate.
- *Base.*—Obtuse.
- *Margin.*—Undulate; having a color of Green Group RHS 139A to 139B.
- *Veins.*—Configuration: Pinnate. Color: Upper Surface: Green Group RHS 139A to 139B. Lower Surface: Green Group RHS 143A to Yellow-Group RHS 147A.
- *Surface quality.*—Leathery.
- *Petiole.*—Length: 5-20 cm. Diameter: 7 mm. Color: The base is White Group RHS 155A, and the upper part is Green Group RHS 143A to 143B.

Roots:
- *Color.*—White.
- *Branching.*—Similar to other *Zantedeschia* varieties.

The Inflorescence and Seeds

Spathe:
- *Size.*—Length (measured from opening to tip): 4-7 cm. Width: 3-4.5 cm. Height: 4-10 cm.
- *Color.*—Upper surface: Varies between White Group RHS 155A and 155D. Lower surface: Varies between White Group RHS 155A and 155D, with variations of Yellow-Green Group RHS 144B and 144D at the base.
- *Vein color.*—Between White Group RHS 155A and 155D.
- *Shape.*—Cupped.
- *Apex.*—Acuminate.
- *Margin.*—Undulate.

Spadix:
- *Size.*—Length: 25-45 mm. Diameter: 2-10 mm.
- *Color.*—Between Yellow-Orange Group RHS 16A and 16C.
- *Position relative to spathe.*—Upright.

Peduncle:
- *Size.*—Length: 10-30 cm. Diameter: 5-11 mm.
- *Color.*—The upper part is between Yellow-Green Group RHS 144A and 144B, and the lower part is Green-White Group RHS 157C.

Reproductive organs:
- *Location of female organs.*—Basal position of the spadix.
- *Location of male organs.*—Upper position of the spadix.
- *Perianth.*—Conspicuous.
- *Stamens.*—Presence: Not visible before pollen release. Number: More than 20. Pollen amount: Similar to 'Picasso' (U.S. Plant Pat. No 15,282). Color: Between White Group RHS 155A and 155B.
- *Anther.*—Shape: Round. Length: Less than 1 mm. Color: Between Yellow-Orange Group RHS 16A and 16C.
- *Filament.*—Length: Less than 1 mm. Color: Between White Group RHS 155A and 155B.
- *Pistils.*—Number: 15 to 30. Length beyond perianth: About 1 mm.
- *Stigma.*—Shape: Round. Size: Less than 1 mm.
- *Style.*—Length: Less than 1 mm. Color: Between Yellow Group RHS 4B and 4D.
- *Ovaries.*—Texture: Smooth. Length: Between 1 to 10 mm. Width: Between 1 to 10 mm. Color: Top color is between Yellow-Green Group RHS 145A and 145D, bottom color is from White Group RHS 155B to Green-White Group RHS 157C.

Seeds:
- *Length.*—4-7 mm.
- *Width.*—3-6 mm.
- *Color.*—Between Yellow-Green Group RHS 150A and 151A.
- *Amount.*—Between 1-60.

General

Disease resistance: No unusual susceptibility to diseases noticed to date.

Pest resistance: No unusual susceptibility to pests noticed to date.

Heat tolerance: No heat tolerance.

Hardiness: Not hardy.

Flowering: Tubers planted in a greenhouse in The Netherlands in February produce inflorescences in April. Tubers planted outdoors in The Netherlands in May produce inflorescences in July.

Lastingness: About two weeks on the plant.

Fragrance: None.

I claim:

1. A new and distinct variety of calla lily plant named 'Helvetia' as herein described and illustrated.

* * * * *